US00PP36576P3

(12) United States Plant Patent
Olesen

(10) Patent No.: US PP36,576 P3
(45) Date of Patent: Apr. 1, 2025

(54) MINIATURE ROSE PLANT NAMED 'Poulty039'

(50) Latin Name: *Rosa hybrida*
Varietal Denomination: Poulty039

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/445,486

(22) Filed: Sep. 8, 2023

(65) Prior Publication Data

US 2024/0107907 P1 Mar. 28, 2024

(30) Foreign Application Priority Data

Sep. 30, 2022 (QZ) ..... PBR 2022/2177

(51) Int. Cl.
*A01H 5/02* (2018.01)
*A01H 6/74* (2018.01)

(52) U.S. Cl.
USPC ..... Plt./116
CPC ..... *A01H 6/749* (2018.05)

(58) Field of Classification Search
USPC ..... Plt./101, 116, 117, 121, 122
See application file for complete search history.

*Primary Examiner* — Susan McCormick Ewoldt
*Assistant Examiner* — Zachariah Allan Kay

(57) ABSTRACT

A new garden rose plant of the Miniature class which has abundant, red and white flowers and attractive foliage. This new and distinct variety has shown to be uniform and stable in the resulting generations from asexual propagation.

2 Drawing Sheets

Botanical designation: *Rosa hybrida.*

Variety denomination: 'Poulty039'.

This application claims priority to Plant Breeder's Rights Application Number 2022/2177, which was filed at the Community Plant Variety Rights Office in the European Union on Sep. 30, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2017 and the resulting seeds were planted in a controlled environment in Fredensborg, Denmark. The new variety, named 'Poulty039', originated as a single seedling from the stated cross.

The new variety may be distinguished from its male pollen parent and female seed parent primarily by the following characteristics. The male pollen parent plant has pink flowers with white stripes while the new variety has red flowers with white stripes. The female seed parent plant has single colour medium red flowers while the new variety has red and white flowers.

The objective of the hybridization of this rose variety was to create a new and distinct variety with unique qualities, such as:

1. Uniform and abundant red and white flowers;
2. Vigorous, but very compact growth when propagated on its own roots;
3. Exceptional disease resistance.

This combination of qualities is not present in previously available commercial cultivars of this type, known to the inventor, and distinguish 'Poulty039' from all other varieties of which we are aware.

As part of the rose development program, Mogens N. Olesen germinated the seeds from the aforementioned hybridization during winter of 2017 and conducted evaluations on the resulting seedlings in a controlled environment in Fredensborg, Denmark. 'Poulty039' was selected in the spring of 2018 by the inventor as a single plant from the progeny of the aforementioned hybridization.

Asexual reproduction of 'Poulty039' by rooted cuttings was first done by Mogens N. Olesen in the nursery in Fredensborg, Denmark in July 2018. This initial and other subsequent asexual propagations conducted in controlled environments have demonstrated that the characteristics of 'Poulty039' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulty039'.

Specifically illustrated in FIG. 1 of the drawings are open flowers viewed from above and the side, flower bud and flowers at various stages of opening, sepals detached revealing reproductive flower parts, and petals detached.

Figure 1:
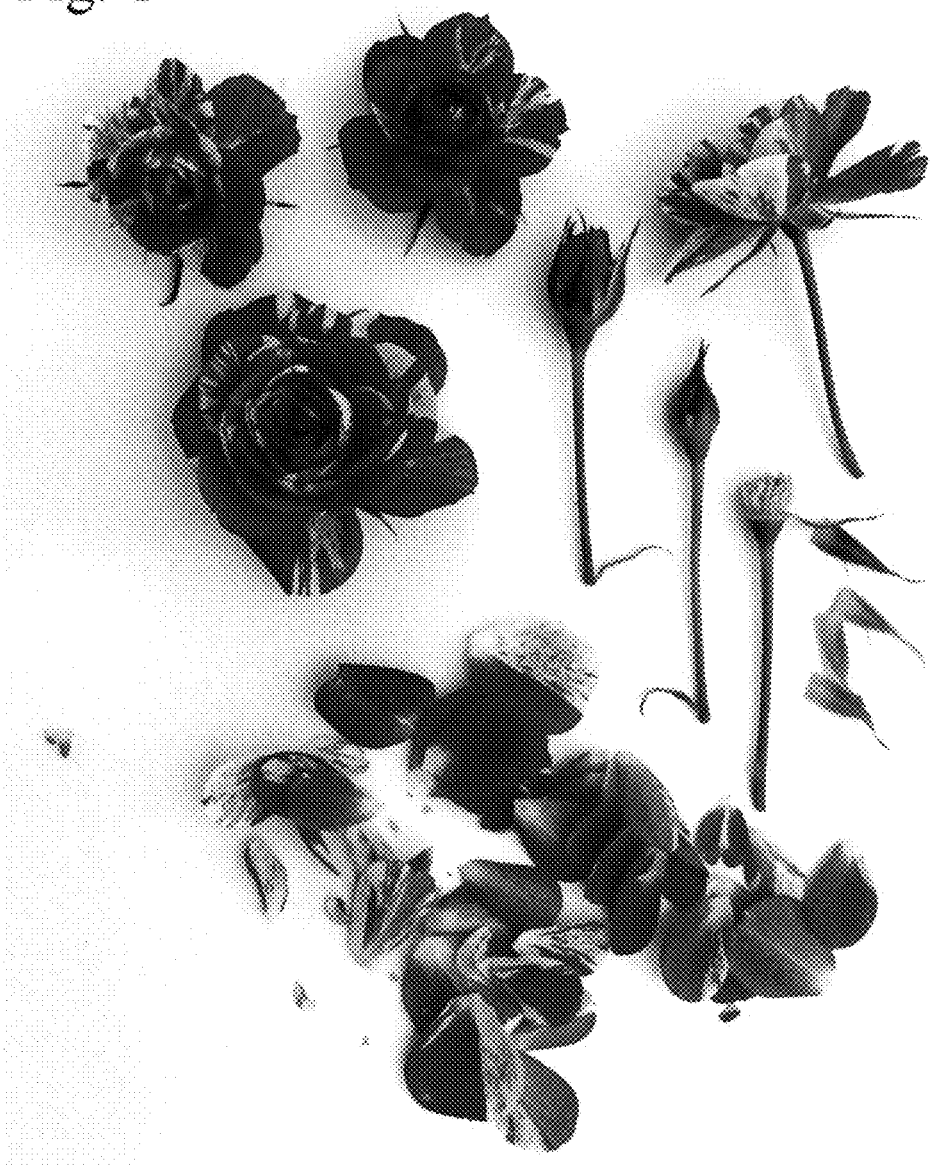
Figure 2:
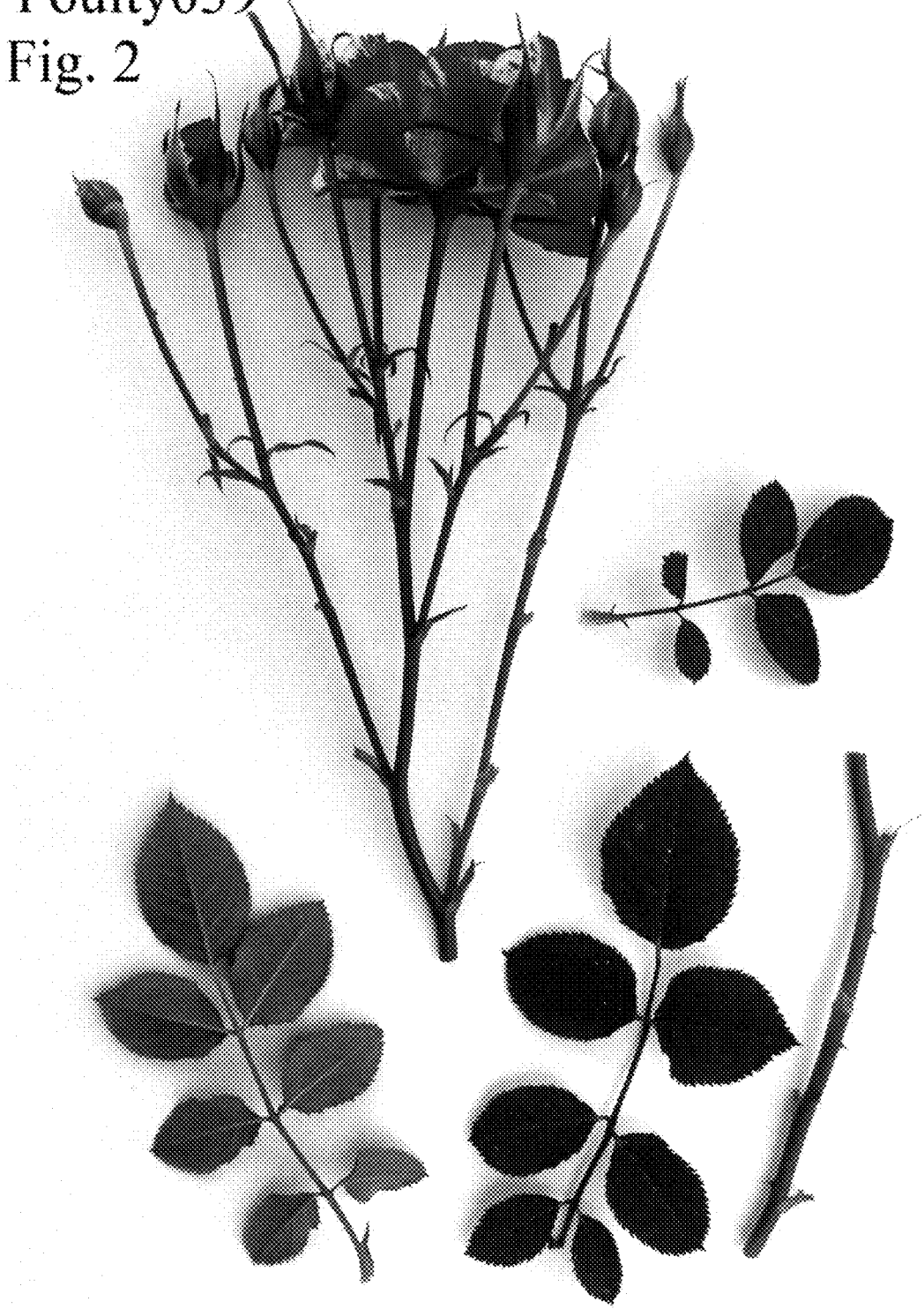

Specifically illustrated in FIG. 2 of the drawings are a cluster of open flowers on the branch, mature leaves, juvenile leaf, and a bare stem exhibiting prickles. Plants shown are 4 months old.

DETAILED DESCRIPTION OF THE VARIETY

The following is a description of 'Poulty039', as observed in its growth in an indoor glasshouse nursery in Odense Denmark. Observed plants are 4 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulty019', U.S. Plant Pat. No. 26,051 are compared to the claimed plant. While 'Poulty039' has 5 to 9 flower per branch, 'Poulty019' has a single flower per branch. The claimed plant has a flower diameter of 60 mm while 'Poulty019' has a flower diameter of 40 mm. Open flowers of 'Poulty039' are generally Red Group 53B with stripes of White Group N155C while 'Poulty019' has a general tonality of Red Group 46A splashed with White Group N155B and Red Group 49A.

FLOWER AND FLOWER BUD

Blooming habit: Continuous.

Flower bud:

*Size.*—Upon opening, 19 mm in length from base of receptacle to end of bud. Bud diameter is 11 mm.

*Bud form.*—Ovoid.

*Bud color.*—As sepals divide petals are Red-Purple Group 61B and White Group 155B.

*Sepal inner surface.*—Color: Yellow-Green Group 146D. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—25 mm long, 6 mm wide.

*Receptacle.*—Texture: Smooth. Size: 5 mm in height, 6 mm wide. Color: Yellow-Green Group 144A. Shape: Funnel.

*Pedicel.*—Surface: Smooth. Length: About 40 mm. Diameter: 2.5 mm on average. Color: Yellow-Green Group 144A. Strength: Strong.

*Peduncle.*—Length: 20 to 90 mm. Diameter: About 2.5 to 3 mm. Color: Yellow-Green Group 144A. Texture: Smooth.

Flower bud development: Flower buds are borne in clusters of about 5 to 9 flower buds per stem. Development as a panicle.

Flower bloom:

*Fragrance.*—Light floral.

*Duration.*—The blooms have a duration on the plant of approximately 21 days. Petals fall cleanly away from plant after flowers have fully matured.

*Size.*—Flower diameter is 60 mm when open. Flower depth is 25 mm.

*Flower shape.*—High centered, double, with a high pointed center which is tightly closed.

*Shape of flower, side view.*—The upper portion is flat. The lower portion is flat.

Petalage: Under normal conditions, flowers have about 41 petals.

General tonality of flower: Open flowers are Red Group 53B. Stripes White Group N155C. After 9 days the main flower colour is Red-Purple Group N57A.

Petal color:

*Upon opening, outer and inner petals.*—Upper surface: Red Group 53B with stripes White Group N155B. Basal zone Yellow Group 4D. Lower surface: Red-Purple Group 61B with streaks of White Group N155B. Basal zone Yellow Group 4D.

*After opening, outer and inner petals.*—Upper surface: Red-Purple Group N66A with a stripe White Group N155B. Basal zone Yellow Group 4D. Lower surface: Red-Purple Group 67C with a stripe White Group N155B. Basal zone Yellow Group 4D.

Petals:

*Petal reflex.*—None.

*Margin.*—Small point at apex. No undulations.

*Shape.*—Broad and elliptic. Apex shape: Rounded. Base shape: Acute.

*Size.*—26 mm (l)×25 mm (w).

*Texture.*—Smooth.

*Thickness.*—Average.

Petaloids:

*Size.*—4 mm (l) by 3 mm (w).

*Quantity.*—About 5.

*Shape.*—Elliptical with an acute base and acute apex.

*Color.*—Yellow-White Group 158C with intonations of Red Group 53B.

Reproductive flower parts:

*Pollen.*—None observed.

*Anthers.*—Size: 2 mm in length. Color: Yellow Group 8C. Quantity: 26 on average.

*Filaments.*—Color: Yellow Group 4B. Length: 4 mm.

*Pistils.*—Length: 4 mm. Quantity: 20 on average.

*Stigmas.*—Color: Yellow-White Group 158D.

*Styles.*—Color: Yellow-White Group 158D.

*Location of stigmas.*—Level in location relative to the length of the filaments and the height of the anthers.

Hips.—None Observed.

PLANT

Plant growth: Upright, bushy. Plants are 35 cm in height, and 30 cm wide.

Stems:

*Color of juvenile growth.*—Yellow-Green Group 144B.

*Color of mature growth.*—Yellow-Green Group 144A.

*Length.*—Canes are about 22 cm from the base of the plant to the flowering portion.

*Diameter.*—About 4 mm.

*Internodes.*—On mature canes about 25 to 30 mm between nodes.

*Surface texture.*—Young wood: Smooth. Older wood: Smooth.

Long prickles:

*Incidence.*—About 4 prickles per 10 cm of stem.

*Size.*—Average length of prickles on mature stems is 4 mm.

*Shape.*—Upper portion is linear. Lower portion is concave.

*Color.*—Juvenile prickles: Greyed-Red Group 181C. Mature prickles: Greyed-Red Group 181C.

Plant foliage:

*Compound leaf.*—115 mm (l)×68 mm (w).

*Quantity.*—3 leaves per 10 cm of stem on average.

*Leaf bearing angle to the stem.*—45 degrees.

*Color of juvenile foliage.*—Upper side: Yellow-Green Group 144A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 6 mm long, 2 mm wide. Quantity: 2 per compound leaf. Shape: Linear, slightly broad based with outward extending apices. Margins: Finely serrated. Color: Yellow-Green Group 144A.

*Petiole*.—Length: 10 to 20 mm. Diameter: 1.5 mm. Upper surface color: Yellow-Green Group 144A. Lower surface color: Yellow-Green Group 144A.

*Rachis*.—Length: 45 to 55 mm Upper surface color: Yellow-Green Group 144A with intonations of Greyed-Red Group 181B. Lower surface color: Yellow-Green Group 144A.

*Leaflet*.—Quantity: Normally 5 or 7 leaflets. Margins: Serrated. Size: Terminal leaflets are about 40 mm long, 30 mm wide. Shape: Generally elliptical. Base: Rounded. Apex: Mucronate. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone.

I claim:

1. A new and distinct variety of rose plant named 'Poulty039' substantially as illustrated and described herein.

* * * * *

'Poulty039'

'Poulty039'